(12) United States Patent
Skilling et al.

(10) Patent No.: US 8,604,421 B2
(45) Date of Patent: Dec. 10, 2013

(54) METHOD AND SYSTEM OF IDENTIFYING A SAMPLE BY ANALYISING A MASS SPECTRUM BY THE USE OF A BAYESIAN INFERENCE TECHNIQUE

(75) Inventors: John Skilling, Kenmare (GB); Keith George Richardson, Derbyshire (GB)

(73) Assignee: Micromass UK Limited, Manchester (GB)

( * ) Notice: Subject to any disclaimer, the term of this patent is extended or adjusted under 35 U.S.C. 154(b) by 0 days.

(21) Appl. No.: 13/640,859

(22) PCT Filed: Apr. 15, 2011

(86) PCT No.: PCT/GB2011/050755
§ 371 (c)(1),
(2), (4) Date: Jan. 9, 2013

(87) PCT Pub. No.: WO2011/128702
PCT Pub. Date: Oct. 20, 2011

(65) Prior Publication Data
US 2013/0200258 A1     Aug. 8, 2013

Related U.S. Application Data

(60) Provisional application No. 61/327,830, filed on Apr. 26, 2010, provisional application No. 61/361,564, filed on Jul. 6, 2010, provisional application No. 61/361,561, filed on Jul. 6, 2010.

(30) Foreign Application Priority Data

Apr. 15, 2010  (GB) .................................. 1006311.3
May 20, 2010  (GB) .................................. 1008421.8
May 21, 2010  (GB) .................................. 1008542.1

(51) Int. Cl.
*H01J 49/00*     (2006.01)

(52) U.S. Cl.
USPC ............................... 250/282; 702/27; 702/28

(58) Field of Classification Search
USPC ........................................ 702/27, 28; 250/282
See application file for complete search history.

(56) References Cited

FOREIGN PATENT DOCUMENTS

WO     2005106453     11/2005

OTHER PUBLICATIONS

Schwarz-Selinger, T. et al.; "Analysis of multicomponent mass spectra applying Bayesian probability theory"; Journal of Mass Spectrometry, 2001; 36: 866-874.
Armstron, N. et al.; "An introduction to Bayesian methods for anlayzing chemistry data; Part 1: An introduction to Bayesian theory and methods"; Cheomometrics and Intelligent Laboratory Systems, vol. 97, No. 2, Jul. 15, 2009; pp. 194-210Elsevier Science Publishers B. V., Amsterdam, NL.
Jain, Anil K., et al; "Statistical Pattern Recognition: A Review"; IEEE Transactions on Pattern Analysis and Machine Intelligence; vol. 22, No. 1, Jan. 2000, pp. 4-37.
Anonymous: "Bayesian inference"; Wikipedia, the free encyclopedia, Jul. 6, 2011, Retrived from internet: URL:http://en.wikipedia.org/wiki/Bayesian_method, 17 pages.
International Search Report and Written Opinion for PCT/GB2011/050755, Form PCT/ISA/210 and PCT/ISA/237, dated Aug. 16, 2011, 8 pages.

*Primary Examiner* — Michael Maskell
(74) *Attorney, Agent, or Firm* — Waters Technologies Corp

(57) ABSTRACT

A method and system for the identification and/or characterization of properties of a sample using mass spectrometry. The method involves producing a measured spectrum of data from a sample using a mass spectrometer, deconvoluting the measured spectrum of data by Bayesian inference to produce a family of plausible deconvoluted spectra of data, inferring an underlying spectrum of data from the family of plausible deconvoluted spectra of data and using the underlying spectrum of data to identify and/or characterize the sample.

24 Claims, 7 Drawing Sheets

METHOD AND SYSTEM OF IDENTIFYING A SAMPLE BY ANALYISING A MASS SPECTRUM BY THE USE OF A BAYESIAN INFERENCE TECHNIQUE

CROSS REFERENCE TO RELATED APPLICATIONS

This application is the National Stage of International application No. PCT/GB 2011/050755, filed on Apr. 15, 2011, which claims priority to and benefit of United Kingdom Patent application No. 1006311.3, filed Apr. 15, 2010; U.S. Provisional Patent Application Ser. No. 61/327,830, filed on Apr. 26, 2010; United Kingdom Patent Application No. 1008421.8, filed May 20, 2010; United Kingdom Patent Application No. 1008542.1, filed May 21, 2010; U.S. Provisional patent application Ser. No. 61/361,561, filed on Jul. 6, 2010; and U.S. Provisional Patent application Ser. No. 61/361,564, filed on Jul. 6, 2010. The contents and teachings of each of these applications are hereby expressly incorporated herein by reference in their entirety.

The invention is in the field of mass spectrometry and more specifically in the field of the analysis and interpretation of data produced by a mass spectrometer.

Mass spectrometers can be used for many applications including identification, characterisation and relative and absolute quantification of proteins, peptides, oligonucleotides, phosphopeptides, polymers and fragments or a mixture of these produced inside the mass spectrometer. One of the current limiting factors in the generation of these results is analysis of the raw data produced from the mass spectrometer. In particular, we are concerned with the isolation and mass measurement of species present in complicated mass spectra.

The data produced by mass spectrometers are complicated due to the ionisation process, the presence of isotopes and the individual characteristics of each instrument.

Current methods for the analysis of raw data produced from mass spectrometers include maximum entropy deconvolution and various algebraic techniques based on inversion, usually by a linear filter.

In attempting to deconvolute the data, linear inversion sharpens individual peaks, which has the unfortunate side effect of introducing "ringing" which damages the reconstruction of complex spectra containing many overlapping peaks. The peaks interfere with each other, and the ringing is liable to produce physically-impossible regions of negative intensity. We consider these techniques to be obsolete.

Maximum entropy (see "Disentangling electrospray spectra with maximum entropy", Rapid Communications in Mass Spectrometry, 6, 707-711) is a nonlinear maximisation inversion, designed to produce an optimal "best possible" result from the given data. In spectrometry, the natural measure of quality of a reconstructed mass spectrum I(M) is the entropy, $$\text{entropy} = -\int I(M) \log I(M) dM$$

Being negative information, this measures the cleanliness of the result, which result (because of the logarithm) is everywhere positive and so physically permissible. Any spectrum $I^*$ other than the maximum entropy spectrum $I^{MaxEnt}$ has more structure, which by definition was not required by the data, so is unreliable.

Modern professional standards demand the quantified error bars that are produced from probabilistic (aka Bayesian) analysis. In order to understand exactly which parts of the maximum entropy result are reliable and which may be unreliable, one needs not just "the best" but also the range of the plausible. To estimate uncertainty, quadratic expansion around the maximum entropy result yields a Gaussian approximation which appears to define the uncertainty on any specified feature. This approach has been implemented but the expansion is deceptive.

Many modern instruments produce high resolution spectra which may be digitised into a correspondingly large number N of bins. As the quality of instrumentation improves, N increases, so that the proportion of signal in any particular bin diminishes as 1/N. The same is true for the variances produced by the quadratic approximation. Hence the size of the error bars around the maximum entropy result decreases more slowly, as the square root of 1/N. The reconstructed signal in a local bin that started comfortably positive as (3±1) percent becomes, at hundred-fold greater resolution, (0.03±0.1) percent, with a substantial probability of being negative. Across the entire spectrum, it becomes almost certain that there will be many negatives in a typical result. But signals are supposed to be positive, so almost all supposedly typical results are impossible when viewed on small scales.

Thus the quadratic approximation breaks down at small scales, where error bars are clearly incorrect so that local structure is not properly quantified. There is therefore a need for an improved deconvolution method with the rigour, power and flexibility to deal with modern instrument performance and applications.

Accordingly, a first aspect of the invention provides a method of identifying and/or characterising at least one property of a sample, the method comprising the steps of producing at least one measured spectrum of data from a sample using a mass spectrometer; deconvoluting the at least one measured spectrum of data by Bayesian inference to produce a family of plausible deconvoluted spectra of data; inferring an underlying spectrum of data from the family of plausible deconvoluted spectra of data; and using the underlying spectrum of data to identify and/or characterise at least one property of the sample.

The method may also comprise the step of identifying the uncertainties associated with underlying spectrum of data, e.g. from the family of plausible deconvoluted spectra of data.

Additionally or alternatively, the deconvolution step may further comprise assigning a prior, for example using a procedure that may comprise one or more, for example at least two steps. The procedure may comprise first assigning a prior to the total intensity and then, for example, modifying the prior to encompass the relative proportions of this total intensity that is assigned to specific charge states.

Optionally, the deconvolution step may further comprise the use of a nested sampling technique.

The procedure may comprise varying predicted ratios of isotopic compositions, for example to identify and/or characterise the at least one property of the sample.

The method may further comprise comparing at least one characteristic of the underlying spectrum of data, e.g. with a library of known spectra, for example to identify and/or characterise the at least one property of the sample.

The method may also comprise comparing at least one characteristic of the underlying spectrum of data, for example with candidate constituents, e.g. to identify and/or characterise the at least one property of the sample.

The deconvolution step comprises the use of importance sampling.

Optionally, the at least one measured spectrum of data may comprise electrospray mass spectral data.

The method may further comprise recording a temporal separation characteristic for the at least one measured spectrum of data and/or may include storing the underlying spectrum of data, e.g. with the recorded temporal separation characteristic, for example on a memory means.

The method may also comprise recording a temporal separation characteristic for the at least one measured spectrum of data, e.g. and using the recorded temporal separation characteristic, for example to identify and/or characterise the or a further at least one property of the sample.

A second aspect of the invention provides a system for identifying and/or characterising a sample, the system comprising: a mass spectrometer for producing at least one measured spectrum of data from a sample; a processor configured or programmed or adapted to deconvolute the at least one measured spectrum of data by Bayesian inference to produce a family of plausible deconvoluted spectra of data and infer an underlying spectrum of data from the family of plausible deconvoluted spectra of data; wherein the processor is further configured or programmed or adapted to use the underlying spectrum of data to identify and/or characterise at least one property of the sample.

In some embodiments, the system further comprises a first memory means for storing the underlying spectrum of data and/or a second memory means on which is stored a library of known spectra. The processor may be further configured or programmed or adapted to carry out a method as described above.

A third aspect of the invention provides a computer program element, for example comprising computer readable program code means, e.g. for causing a processor to execute a procedure to implement the method described above.

The computer program element may be embodied on a computer readable medium.

A fourth aspect of the invention provides a computer readable medium having a program stored thereon, for example where the program is to make a computer execute a procedure, e.g. to implement the method described above.

A fifth aspect of the invention provides a mass spectrometer suitable for carrying out, or specifically adapted to carry out, a method as described above and/or comprising a program element as described above a computer readable medium as described above.

A sixth aspect of the invention provides a retrofit kit for adapting a mass spectrometer to provide a mass spectrometer as described above. The kit may comprise a program element as described above and/or a computer readable medium as described above.

Embodiments of the invention will now be described by way of example only with reference to the accompanying drawings in which.

Figure 1:
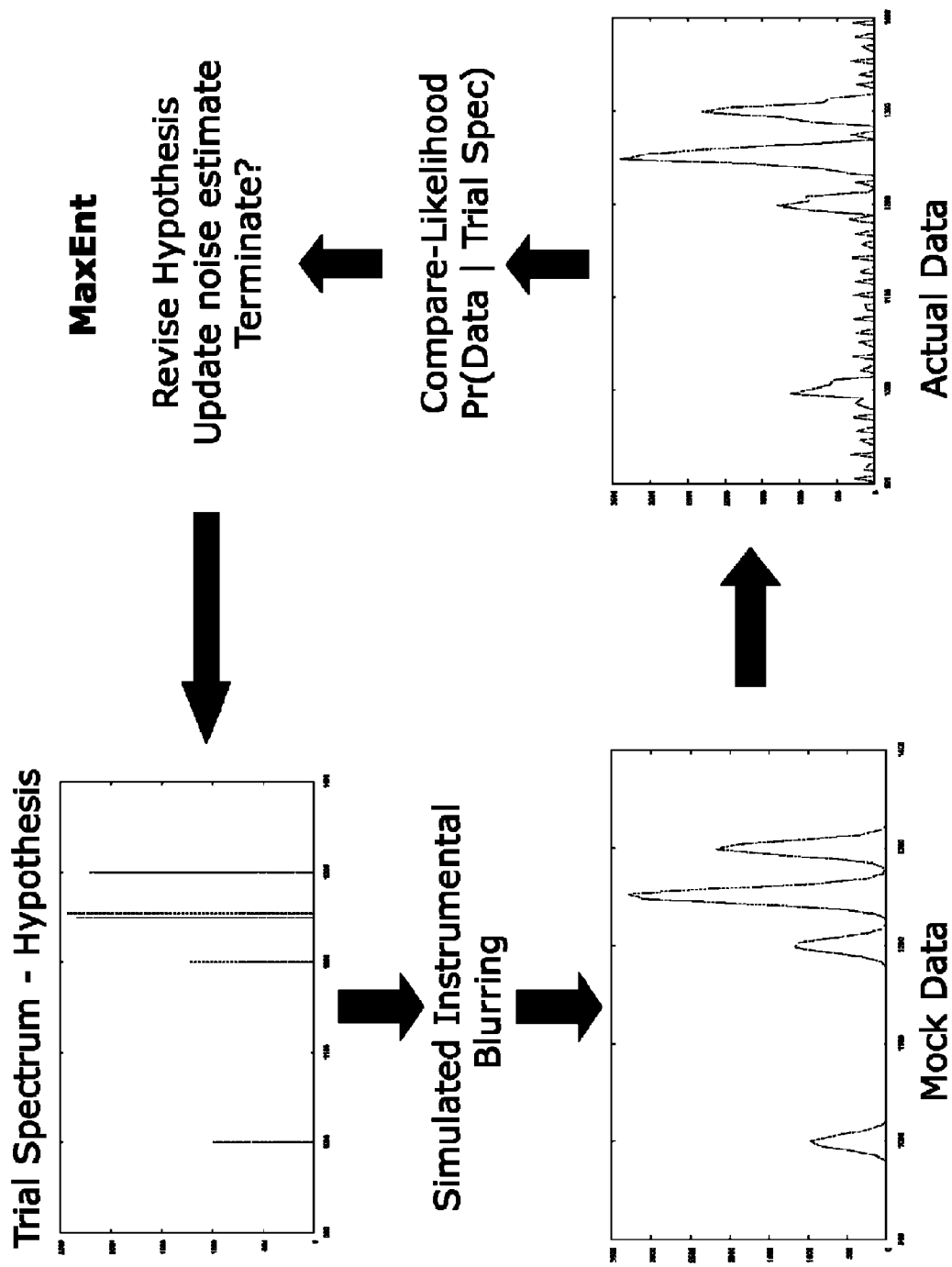
FIG. 1 is a flowchart depicting the workflow for the prior art, maximum entropy deconvolution.
Figure 2:
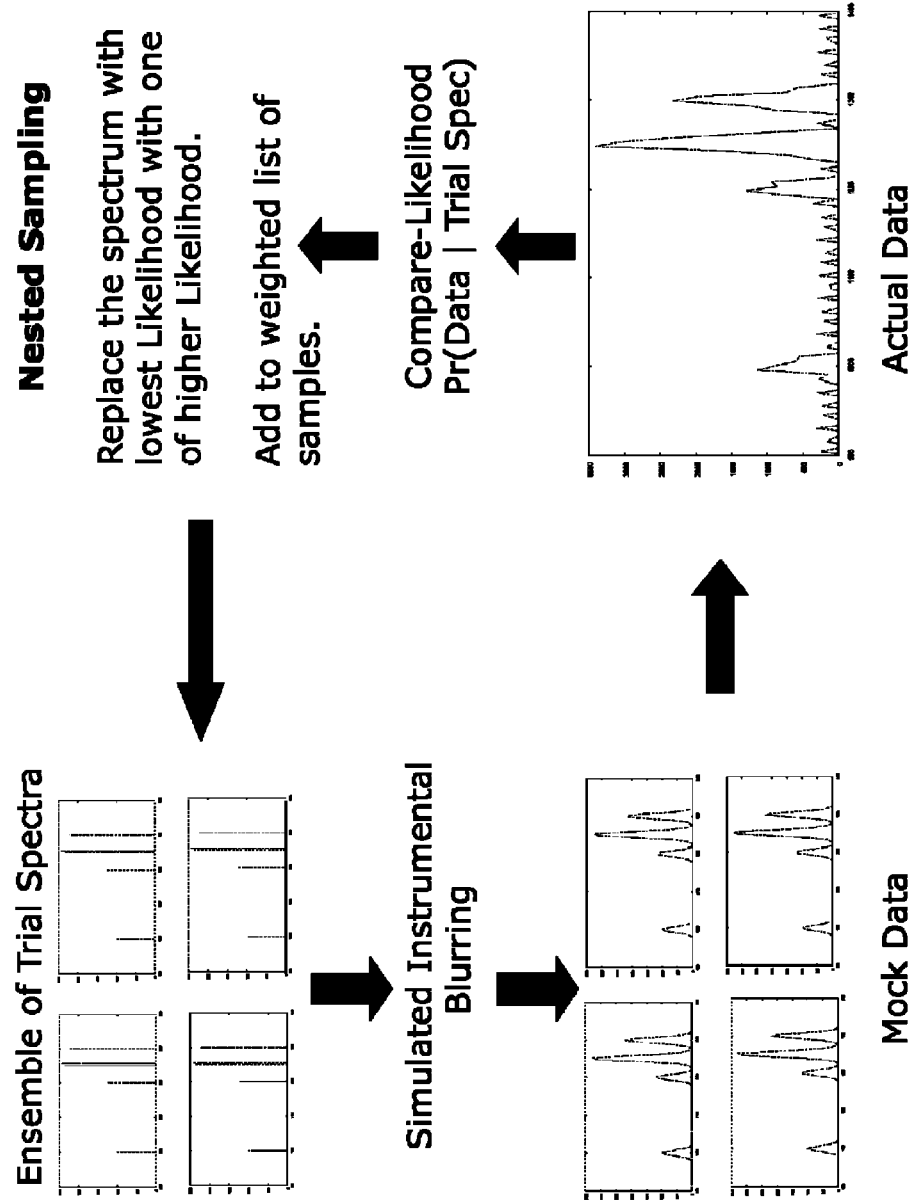
FIG. 2 is a flowchart depicting the workflow for an embodiment of the present invention.

In the preferred embodiment a method and apparatus for the deconvolution of mass spectral data is provided. This method preferably uses Bayesian Inference implemented using nested sampling techniques in order to produce improved deconvoluted mass spectral data.

Bayesian inference is the application of standard probability calculus to data analysis, taking proper account of uncertainties.

Bayesian inference does not provide absolute answers. Instead, data modulate our prior information into posterior results. Good data is sufficiently definitive to over-ride prior ignorance, but noisy or incomplete data is not. To account for this, the rules of probability calculus require assignment of a prior probability distribution over a range sufficient to cover any reasonable result. A mass range within which the target masses must lie might be specified, and, less obviously, information about how many target masses are reasonable could be provided.

Prior information must be specified in enough detail to represent expectations about what the target spectrum—in the preferred embodiment a spectrum of parent masses—might be, before the data are acquired. One specifies an appropriate range of targets T through a probability distribution prior($T$)=prior probability of target $T$ known in Bayesian parlance as "the prior".

There is a huge number of possible targets, depending on how many masses may be present, and the myriad different values those masses and their associated intensities could take. Practical instrumentation usually has a few more calibration parameters as well, which adds to the uncertainty in the target. Nevertheless, it is assumed that the instrument can be modelled well enough that average data (known as mock data) can be calculated for any proposed target (and any proposed calibration). Actual data will be noisy, and won't fit the mock data exactly. The noise is part of the presumed-known instrumental characteristics, so that the misfit between actual and mock data lets us calculate, as a probability, how likely the actual data were. This probability is known as "the likelihood"

Lhood($T$)=Prob(actual data $D$ GIVEN proposed target $T$)

which is the other half of the Bayesian inputs (the other being the prior).

The product law of probability calculus then gives a joint distribution $$\underset{\text{Joint}(T)}{\text{Prob}(D \text{ AND } T)} = \underset{\text{prior}(T)}{\text{Prob}(T)} \times \underset{\text{Lhood}(T)}{\text{Prob}(D \text{ GIVEN } T)}$$

In the presence of complicated data, the possibility of processing the joint distribution through algebraic manipulation rapidly fades, so that it needs to be computed numerically as an ensemble of typically a few dozen plausible targets $T_1$, $T_2$, ..., $T_n$, accompanied by weights $w_1$, $w_2$ ... $w_n$ that need not be uniform.

Methods which yield these weighted ensembles are required. These methods will provide the joint distribution.

Using the probability product law the other way round gives the Bayesian outputs $$\underset{\text{Joint}(T)}{\text{Prob}(D \text{ AND } T)} = \underset{\text{Evidence}}{\text{Prob}(D)} \times \underset{\text{Posterior}(T)}{\text{Prob}(T \text{ GIVEN } D)}$$

The "evidence" measures how well the prior model managed to predict the actual data, which assesses the quality of the model against any alternative suggestions. It's evaluated as the sum of the weights. The "posterior" is the inference about what the target was—which is usually the user's primary aim. It's evaluated as the ensemble of plausible targets, weighted by the relative w's.

The joint distribution thus includes both halves, evidence and posterior, of Bayesian inference. Nested sampling is the preferred method for the computation of this distribution.

It is easy to take random samples from the prior alone, ignoring the data. Each sample target has its likelihood value, so in principle it might be possible to find the good targets of high likelihood by taking random proposals. The difficulty is that there's too much choice. Suppose a mass spectrum has 100 lines each located to 100 ppm (1 in 10000 accuracy). Only one trial in $10000^{100}=10^{400}$ will get to the right answer. Obviously, computing $10^{400}$ samples would be prohibitively time consuming and is therefore impractical.

That example illustrates that the posterior is exponentially tighter than the prior. Every relevant bit of data halves the number of plausible results, so compresses by a factor of 2. Although the number of relevant bits may be considerably less than the size of the (somewhat redundant) dataset, it's still likely to be hundreds or thousands. To accomplish exponential compression, it's essential to bridge iteratively from prior to posterior. A single step can compress by O(1), say a factor of 2, without undue inefficiency, so that the required compression can be achieved in a feasible number (say hundreds or thousands) of iterations.

In the preferred embodiment, the required deconvolution is of electrospray mass spectrometry data. In this case, the data are complicated by the presence of variable charge attached to each target mass. Nested Sampling helps us to accomplish the required probability computation, even in the face of the extra uncertainty of how the signals from each parent mass are distributed over charge.

Nested Sampling (see "Nested sampling for general Bayesian computation", Journal of Bayesian Analysis, 1, 833-860 (2006)) is an inference algorithm specifically designed for large and difficult applications. In mass spectrometry, iteration is essential because single-pass algorithms are inherently incapable of inferring a spectrum under the nonlinear constraint that intensities must all be positive. Nested-sampling iterations steadily and systematically extract information (also known as negative entropy) from the data and yield mass spectra with ever-closer fits.

Although capable of proceeding to a final "maximum likelihood" solution, the algorithm is in practice stopped when it has acquired enough information to define the distribution of spectra that are both intrinsically plausible and offer a probabilistically correct fit to the data. After all, any single solution would be somehow atypical, whereas professional standards demand that results are provided with proper estimates of the corresponding uncertainties, which can only be achieved through the ensemble.

Although nested sampling can in principle cope with arbitrary likelihood and arbitrary prior, it remains advantageous to choose an appropriate prior (the likelihood function being fixed by the responses as specified by the equipment manufacturer). If the assigned prior is not appropriate, the data will be un-necessarily surprising, which shows up as an un-necessarily low evidence value, which in turn takes longer (possibly hugely longer) to compute.

Particularly in electrospray, it's easy to choose a prior that's not appropriate. This is because a given mass M may carry charges Z varying over a substantial range, perhaps anywhere from 10 to 20 for a mass of 20000. We need a prior on this distribution, because we must be able to predict mock data. Given that the charge states appear separately in the observed M/Z data, it might seem reasonable to assign a separate prior for each charge state: for example $$\text{Prior for } (Z=10 \text{ and } Z=11 \text{ and } \ldots Z=20) =$$
$$(\text{prior for } Z=10) \times (\text{prior for } Z=11) \times \ldots \times (\text{prior for } Z=20).$$

However it then becomes very unlikely that a mass will appear with a low total signal strength, because all 11 individual strengths have to be small before the total can be small. This is not usually expected: real spectra usually have many weak signals and this, according to the prior, is extremely improbable. Hence nested sampling runs much too slowly, in practice freezing onto any of a variety of wrong answers.

It is far better to use a two-stage prior for the signal strengths. First, a master prior is assigned to the total intensity I. In one embodiment this may be Cauchy $$\text{Prior}(I) \propto 1/(I^2 + \text{constant}).$$

With total intensity fixed, the subsidiary prior on charge state becomes a prior on the relative proportions assigned to specific charges. In one embodiment this may be uniform:

$$\text{Prior for}(Z=10 \text{ and } Z=11 \text{ and} \ldots Z=20 \text{ GIVEN } I)=\text{constant}.$$

In another embodiment, the charge-state signals could be correlated and/or weighted by charge. With this sort of two-stage prior, the algorithm no longer freezes inappropriately.

The immediate output from nested sampling is an ensemble of several dozen typical spectra, each in the form of a list of parent masses. These masses have intensities which are separately and plausibly distributed over charge. Just as in statistical mechanics (which helped to inspire nested sampling), the ensemble can be used to define mean properties together with fluctuations. In this way, nested-sampling results can be refined to a list of reliably inferred masses, with proper error bars expressing statistical uncertainty, and full knowledge of how each mass relates to the data.

Individual parent masses are accompanied by, maybe dominated by, their isotope distributions. In typical deconvolution, the isotopic composition of a given mass M is fixed at some ratio pattern $$\text{Parent:Isotope\#1:Isotope\#2:}$$

given by an average chemical composition. In the standard embodiment of the invention, mock data is produced from trial parent masses by convolution with this mass-dependent isotope distribution, expanded to cover the charge states, and finally convolved with the instrumental peak shape.

Another complication in the analysis of mass spectral data is the presence of a variety of naturally occurring or artificially introduced isotopic variants of the elements comprising the molecules being analyzed. Furthermore, deviations from the assumed pattern can occur for particular compositions. These induce harmonic artefacts at wrong masses, as the probability factors try to fit the data better. In one embodiment of the present invention, a distribution $$\text{Prior for}(\text{Parent},\text{Isotope\#1},\text{Isotope\#2}, \ldots )$$

of isotope proportions may be used. This distribution should be peaked around the average, but also allow appropriate flexibility.

For each dataset, an appropriate model of the instrumental peak shape corresponding to an isotopically pure species can be used. For example, a fixed full width at half maximum might be used for quadrupole data, whereas a fixed instrument resolution could be specified for TOF data.

In a further embodiment, the computation may be reformulated by using "importance sampling" to reduce the computational load. This statistical method has the side-effect of improving the accuracy and fidelity of the results obtained. In the original embodiment, each parent has a uniform prior over its mass:

prior(M)=flat and the given likelihood Lhood(M) is used directly. If this is the only mass present, this likelihood yields the joint distribution Joint(M)=prior(M)×Lhood(M)

which represents the very simplest (single-parent) deconvolution.

But it is also possible to write

Joint(M)=density(M)×(prior(M)×Lhood(M)/density(M))

for arbitrary density. Instead of starting with the prior and applying the likelihood, it is also possible to start with the new density and apply the modified likelihood Modified(M)=prior(M)×Lhood(M)/density(M)

If the density removes structure from the likelihood and modifies it to something less sharp and spiky, this will reduce the computational load.

As it happens, there is a natural density to hand. Most mass spectrometry data is essentially linear, so that Mock data=(Linear matrix)·(Target masses)

Applying that linear matrix in reverse (as its transpose) to the real data yields a candidate density=(transpose of Linear matrix)·(real data)

This density is a doubly-blurred version of the true target, blurred once in the instrument and by the multiplicity of charge state, and again via the transpose. Nevertheless, the computational task of deconvolving it is often very much less than having to start from scratch, with a flat prior. Such a program runs much more quickly and precisely.

In another embodiment of the invention, the data being deconvoluted may come from a TOF, Quadrupole, FTICR, Orbitrap, Magnetic sector, 3D Ion trap or Linear ion trap. In each of these instances, an appropriate model of peak shape and width as a function of mass to charge ratio and intensity should be used.

In a further embodiment of the invention, the data being deconvolved may be produced from ions generated by an ion source from ESI, ETD etc. . . . .

In each of these instances, the distribution of charge states is characteristic of the technique. For example, ions produced by Maldi ionization are usually singly charged, while electrospray produces a distribution over a large range of charge states for large molecules.

In a yet further embodiment of the invention, the data being processed may be from species that have been separated using a separation device selected from the group including but not limited to: LC, GC, IMS, CE, FAIMS or combinations of these or any other suitable separation device. In each case, the distribution over the extra analytical dimensions is treated similarly to the distribution over charge states as described above.

In a still further embodiment of the invention, the data being deconvolved may be produced from a sample containing proteins, peptides, oligonucleotides, carbohydrates, phosphopeptides, and fragments or a mixture of these. In each case, the isotope model or models employed should reflect the composition of the type of sample being analyzed. As part of this embodiment, trial masses may be assigned individual molecule types.

Figure 3:
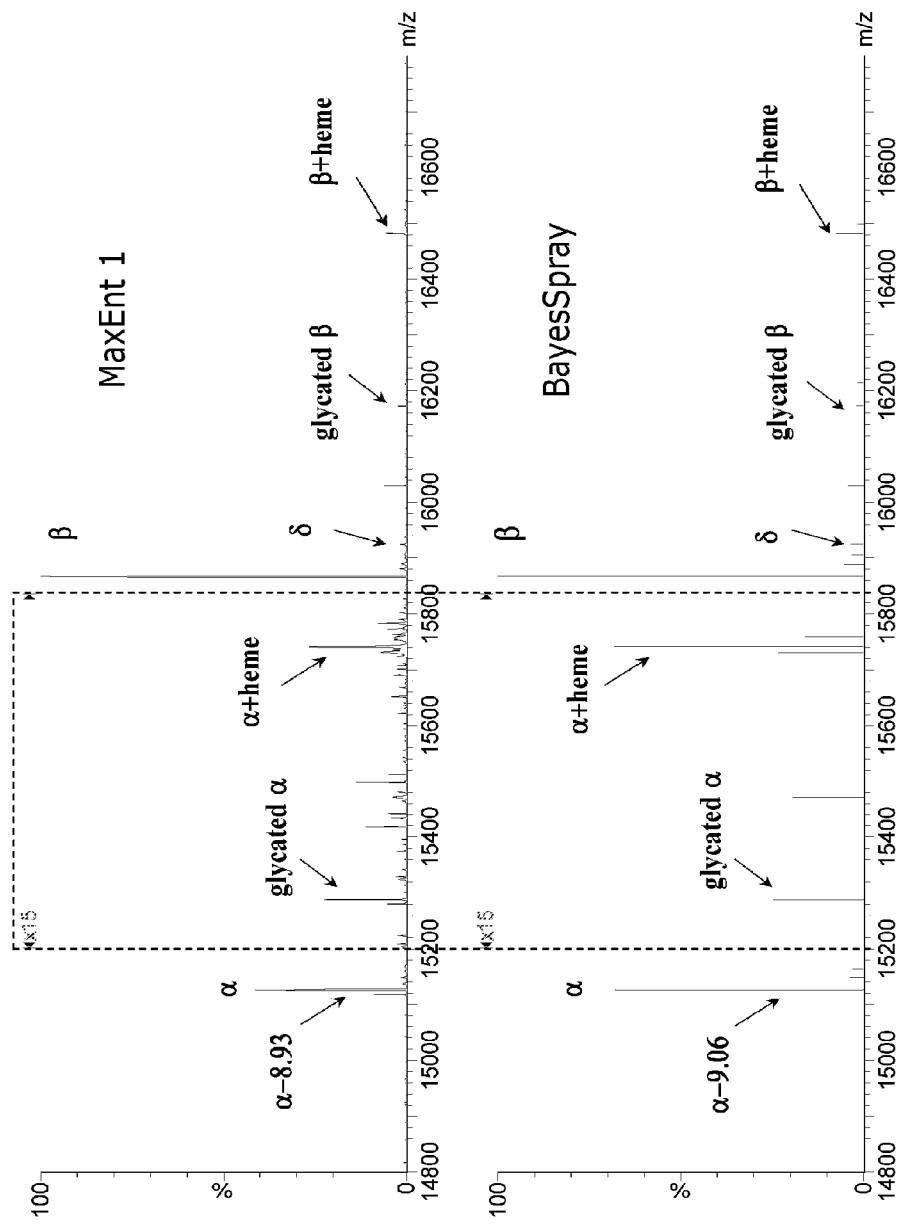
FIG. 3 shows annotated deconvoluted spectra of a mixture of proteins analysed using MaxEnt and Nested Sampling.
Figure 4:
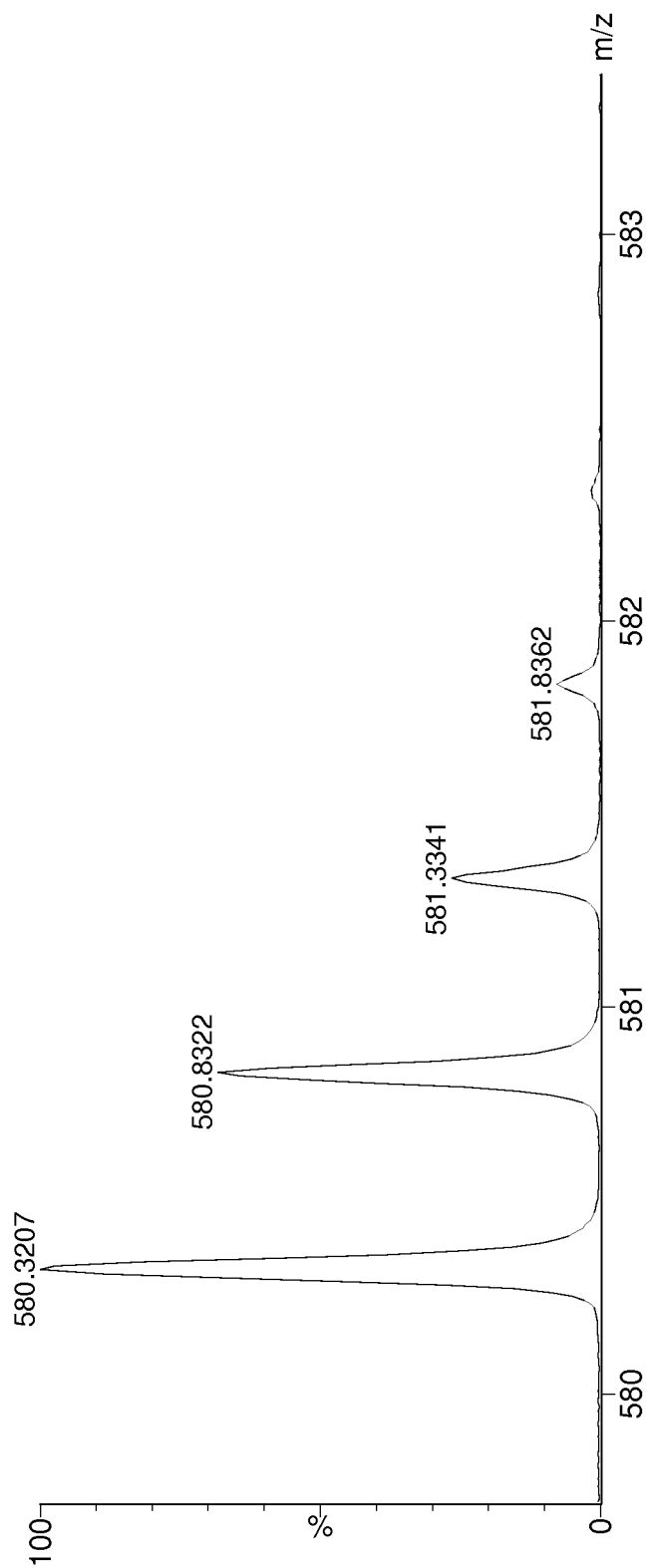
FIG. 4 shows a spectrum containing the isotope cluster from a single parent mass.

FIG. 3 demonstrates the ability of BayesSpray to detect minor components such as the δ-chain and glycated α- and β-chains in an infused sample of human hemoglobin. In addition, the unresolved variant α-chain is separated by the algorithm, and the mass difference is measured with an accuracy comparable to the MaxEnt 1 result. Also visible, but not annotated, are sodium and potassium adducts and the variant α-chain plus heme. Note that although the spectra are remarkably similar, and all annotated minor components are present in both spectra, the baseline in the magnified region is considerably cleaner in the new result. This is a typical distinction between MaxEnt and BayesSpray reconstructions of even the most complex intact protein spectra.

Figure 5:
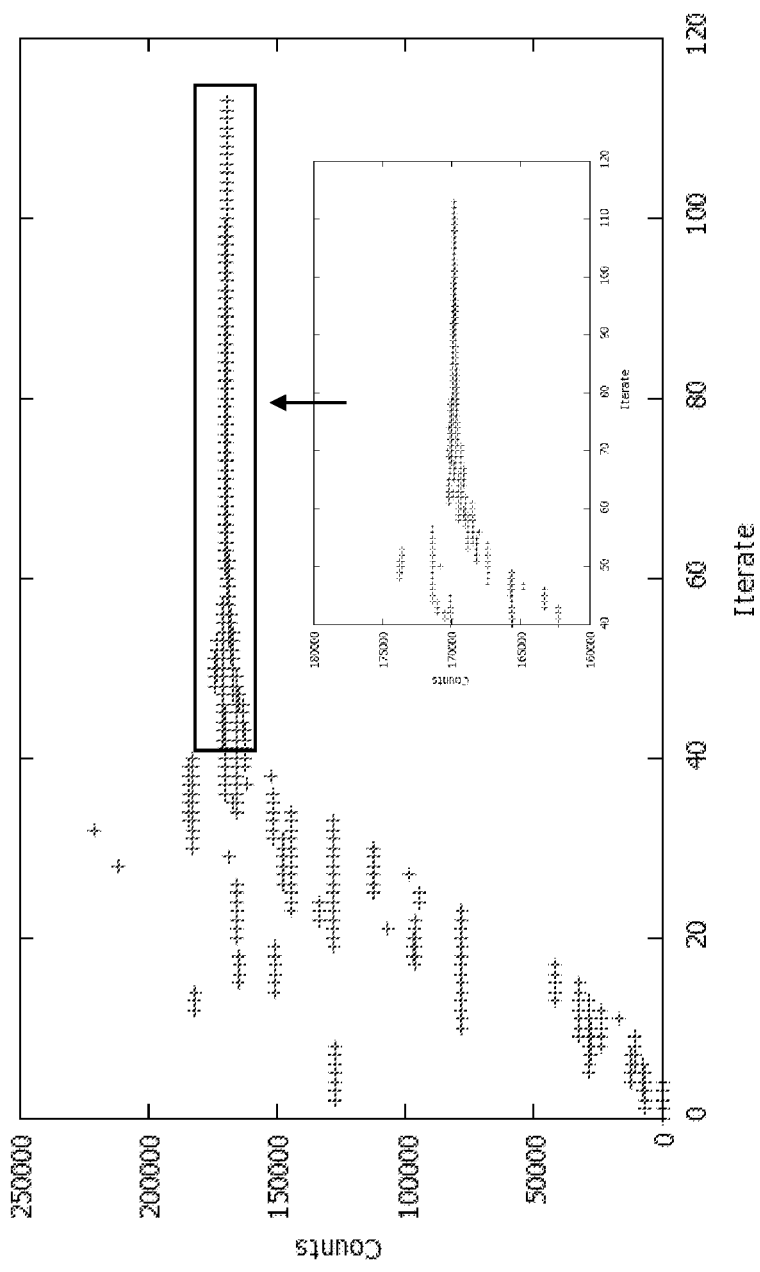
FIGS. 5 and 6 show the intensities and masses from an ensemble of five samples through 114 iterations of nested-sampling, using the data of FIG. 4.
Figure 6:
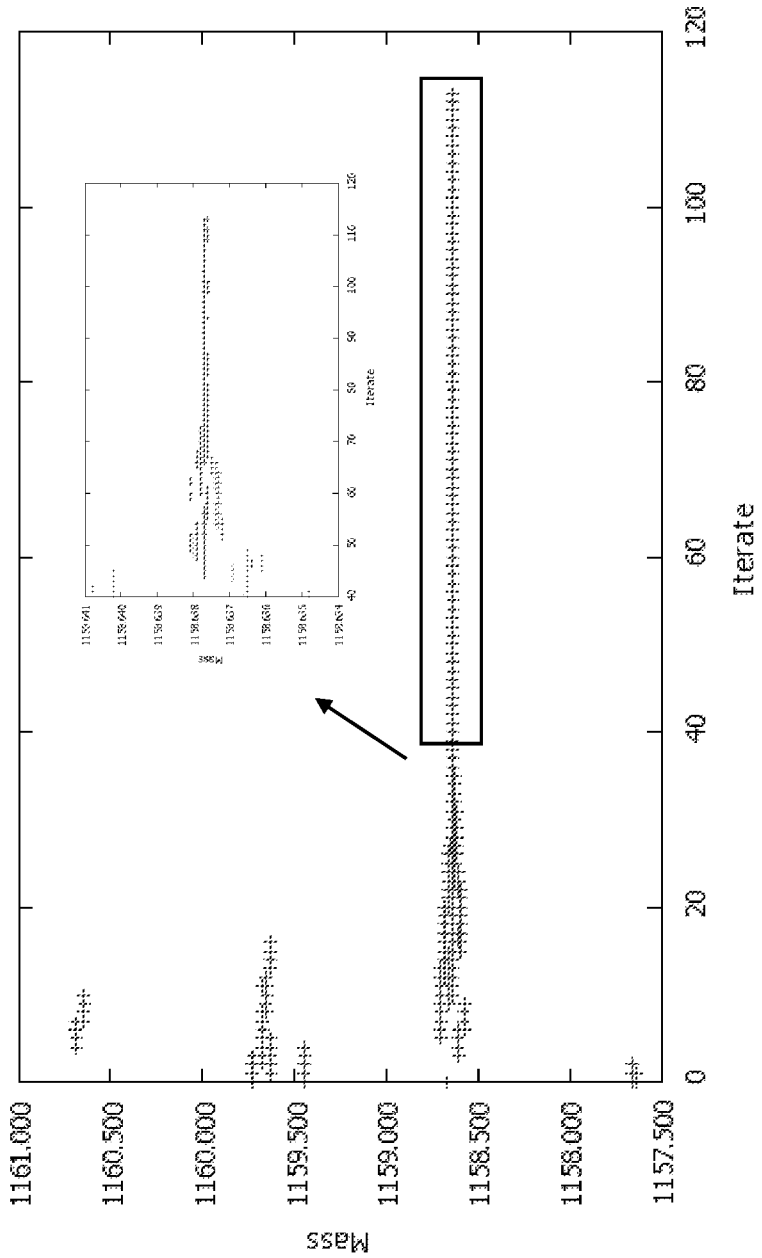

FIGS. 5 and 6 illustrate steady and systematic convergence towards fitting the data, ultimately arriving at the maximum-likelihood solution.

Figure 7:
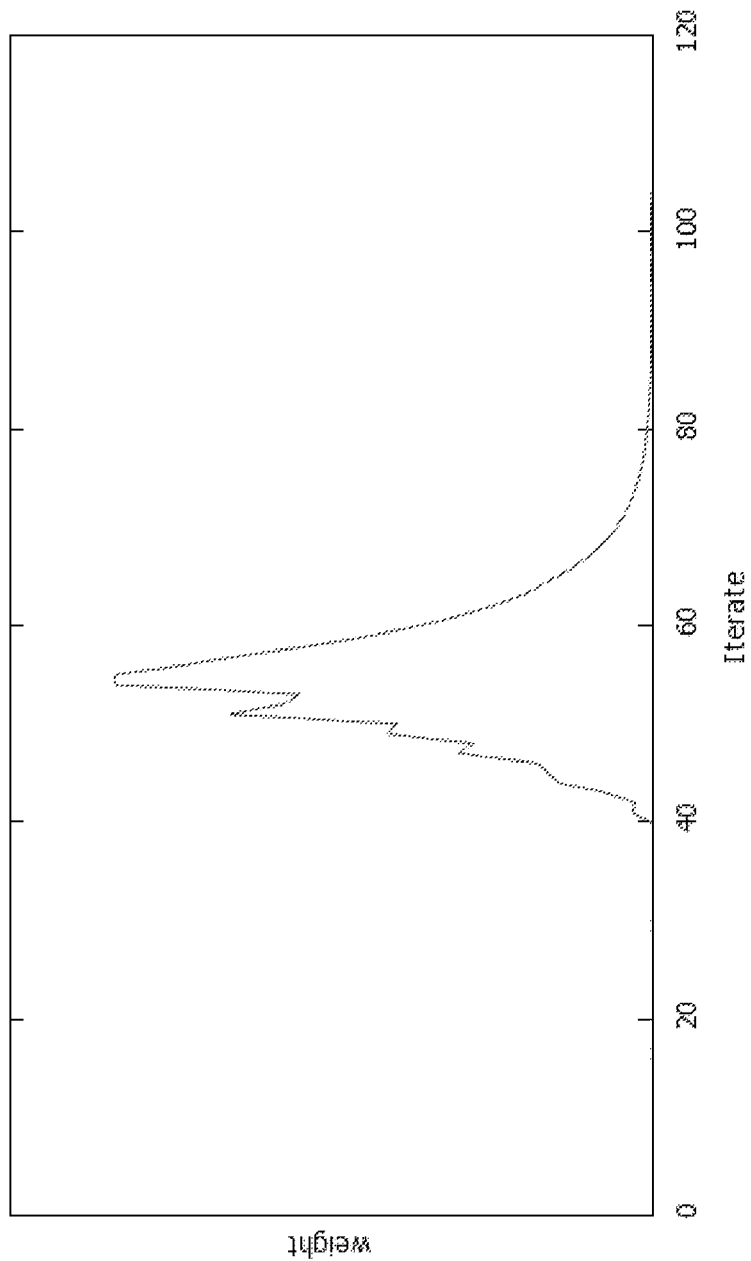
FIG. 7 displays the corresponding probabilistic weights.

The weights shown in FIG. 7 peak around iterates 50-60, after which rising likelihood can no longer overcome the increasing irrelevance of the ever-tinier neighbourhood of the maximum-likelihood point (which in general need not be at all typical of the posterior as a whole).

It is through these weights that nested sampling arrives at its results, with mean values deriving from inter-sample averages, and uncertainty deriving from inter-sample variability.

It will be appreciated by those skilled in the art that any number of combinations of the aforementioned features and/or those shown in the appended drawings provide clear advantages over the prior art and are therefore within the scope of the invention described herein.

The invention claimed is:

1. A method of identifying or characterising at least one property of a sample, the method comprising the steps of:
   a. producing at least one measured spectrum of data from a sample using a mass spectrometer;
   b. deconvoluting the at least one measured spectrum of data by Bayesian inference to produce a family of plausible deconvoluted spectra of data;
   c. inferring an underlying spectrum of data from the family of plausible deconvoluted spectra of data; and
   d. using the underlying spectrum of data to identify or characterise at least one property of the sample.

2. The method of claim 1 further comprising the step of identifying the uncertainties associated with underlying spectrum of data from the family of plausible deconvoluted spectra of data.

3. The method of claim 1 wherein the deconvolution step further comprises assigning a prior using a procedure comprising at least two steps.

4. The method of claim 3, wherein the procedure comprises first assigning a prior to the total intensity and then modifying the prior relative to the proportions for specific charge states.

5. The method of claim 1, wherein the deconvolution step further comprises the use of a nested sampling technique.

6. The method of claim 1, wherein the procedure comprises varying predicted ratios of isotopic compositions to identify or characterise the at least one property of the sample.

7. The method of claim 1 further comprising comparing at least one characteristic of the underlying spectrum of data with a library of known spectra to identify or characterise the at least one property of the sample.

8. The method of claim 1 further comprising comparing at least one characteristic of the underlying spectrum of data with candidate constituents to identify or characterise the at least one property of the sample.

9. The method of claim 1, wherein the deconvolution step comprises the use of importance sampling.

10. The method of claim 1, wherein the at least one measured spectrum of data comprises electrospray mass spectral data.

11. The method of claim 1, further comprising recording a temporal separation characteristic for the at least one measured spectrum of data and storing the underlying spectrum of data with the recorded temporal separation characteristic on a memory means.

12. The method of claim 1, further comprising recording a temporal separation characteristic for the at least one measured spectrum of data and using the recorded temporal separation characteristic to identify or characterise the or a further at least one property of the sample.

13. A system for identifying or characterising a sample, the system comprising:
  a. a mass spectrometer for producing at least one measured spectrum of data from a sample;
  b. a processor configured or programmed or adapted to deconvolute the at least one measured spectrum of data by Bayesian inference to produce a family of plausible deconvoluted spectra of data and infer an underlying spectrum of data from the family of plausible deconvoluted spectra of data; and
  wherein the processor is further configured or programmed or adapted to use the underlying spectrum of data to identify or characterise at least one property of the sample.

14. The system of claim 13 further comprising a first memory means for storing the underlying spectrum of data.

15. The system of claim 14 further comprising a second memory means on which is stored a library of known spectra.

16. The system of claim 15, wherein the processor is further configured or programmed or adapted to carry out a method according to any one of claims 1 to 12.

17. A computer program element comprising computer readable program code means for causing a processor to execute a procedure to implement the method of claim 1.

18. The computer program element of claim 17 embodied on a computer readable medium.

19. A computer readable medium having a program stored thereon, where the program is to make a computer execute a procedure to implement the method of claim 1.

20. A mass spectrometer suitable for carrying out, or specifically adapted to carry out, a method according to claim 1.

21. A retrofit kit for adapting a mass spectrometer to provide a mass spectrometer suitable for carrying out, or specifically adapted to carry out, a method according to claim 1, the kit comprising a computer program element including computer readable program code means for causing a processor to execute a procedure to implement that method.

22. The retrofit kit of claim 21, wherein the computer program element is embodied on a computer readable medium.

23. A mass spectrometer comprising the program element of claim 17.

24. A mass spectrometer comprising a computer readable medium according to claim 19.

* * * * *